United States Patent [19]

Das et al.

[11] Patent Number: 5,260,448

[45] Date of Patent: Nov. 9, 1993

[54] METHOD FOR PREPARING 7-OXABICYCLOHEPTYL SUBSTITUTED HETEROCYCLIC AMIDE PROSTAGLANDIN ANALOGS USEFUL IN THE TREATMENT OF THROMBOTIC AND VASOSPASTIC DISEASE

[75] Inventors: Jagabandhu Das, Hamilton Square, N.J.; David Kronenthal, Yardley, Pa.

[73] Assignee: E. R. Squibb & Sons, Inc., Princeton, N.J.

[21] Appl. No.: 900,383

[22] Filed: Jun. 18, 1992

Related U.S. Application Data

[63] Continuation-in-part of Ser. No. 846,842, Mar. 6, 1992, abandoned.

[51] Int. Cl.⁵ .................................. C07D 263/32
[52] U.S. Cl. .................................. 548/236; 546/275; 546/269; 548/311.7; 548/525; 549/463
[58] Field of Search ............... 548/236; 546/269, 275

[56] References Cited

U.S. PATENT DOCUMENTS 5,100,889  3/1992  Misra et al. ............... 548/236
5,158,967  10/1992  Hall ............................ 548/236

OTHER PUBLICATIONS

CA 114:164202r, Preparation of . . . vasorelaxants, Misra, p. 776, 1991.

*Primary Examiner*—Mary C. Lee
*Assistant Examiner*—Joseph K. McKane
*Attorney, Agent, or Firm*—Burton Rodney

[57] ABSTRACT

A method is provided for preparing 7-oxabicycloheptyl substituted heterocyclic amide prostaglandin analogs which are thromboxane $A_2$ ($TXA_2$) receptor antagonists or combined thromboxane $A_2$ receptor antagonists/thromboxane synthetase inhibitors useful, for example, in the treatment of thrombotic and/or vasospastic disease, wherein a vinyl bromide of the formula, for example,

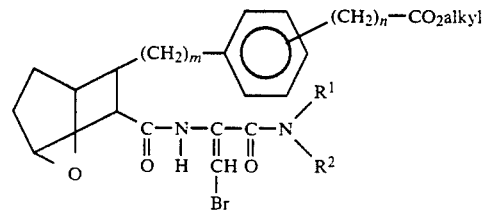

wherein m, n, $R^1$ and $R^2$ are as defined herein is treated with a cyclizing agent to form the corresponding oxazole.

28 Claims, No Drawings

METHOD FOR PREPARING 7-OXABICYCLOHEPTYL SUBSTITUTED HETEROCYCLIC AMIDE PROSTAGLANDIN ANALOGS USEFUL IN THE TREATMENT OF THROMBOTIC AND VASOSPASTIC DISEASE

This is a continuation-in-part of application Ser. No. 846,842, filed Mar. 6, 1992, now abandoned.

DESCRIPTION OF THE INVENTION

The present invention relates to a method for preparing 7-oxabicycloheptyl substituted heterocyclic amide prostaglandin analogs which are thromboxane $A_2$ (TXA$_2$) receptor antagonists or combined thromboxane $A_2$ receptor antagonists/thromboxane synthetase inhibitors useful, for example, in the treatment of thrombotic and/or vasospastic disease, and described in U.S. application Ser. No. 540,026, filed Jun. 18, 1990 now U.S. Pat. No. 5,100,889, issued Mar. 31, 1991 (which is incorporated herein by reference), and to a method for preparing intermediates for use in the above method.

In accordance with the present invention, a method is provided for preparing oxazoles of the structure I

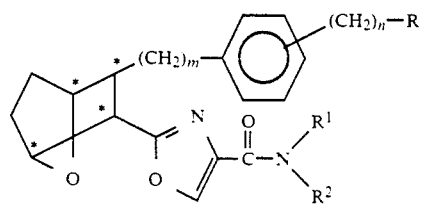

and including all stereoisomers thereof, wherein
m is 1, 2 or 3; n is 0, 1, 2, 3 or 4;
$(CH_2)_n$ is unsubstituted or substituted with one or two lower alkyl groups;
R is $CO_2H$, $CO_2$lower alkyl or $CO_2$alkali metal;
$R^1$ is hydrogen, lower alkyl, lower alkenyl, lower alkynyl, aralkyl, aryl, cycloalkyl, cycloalkylalkyl, cycloheteroalkyl, cycloheteroalkylalkyl, heteroaryl or heteroarylalkyl, or amide

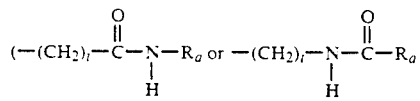

wherein t is 1 to 12 and $R_a$ is lower alkyl, aryl, cycloalkyl, or cycloalkylalkyl), each of $R^1$ being unsubstituted or optionally substituted with a lower alkyl, aryl, cycloalkyl, or cycloalkylalkyl group;
$R^2$ is hydrogen, lower alkyl, aryl, or aralkyl; or
$R^1$ and $R^2$ together with the nitrogen to which they are linked may form a 5- to 8- membered ring;
wherein a vinyl bromide of the structure

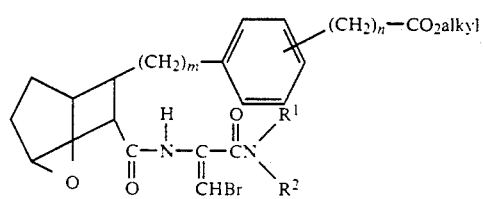

is treated with a cyclizing agent, such as a metal carbonate, for example, cesium carbonate, in the presence of an inert organic solvent, such as dioxane to form the desired oxazole ester I wherein R is $CO_2$alkyl.

The oxazole ester may be converted to the corresponding alkali metal salt such as sodium, potassium or lithium salt, preferably the sodium salt, by treating oxazole I wherein R is $CO_2$alkyl with an alkali metal hydroxide to form the alkali metal salt.

The oxazole salt may then be converted to the free acid by treating the salt with an acid such as hydrochloric acid or oxalic acid.

In addition, in accordance with the present invention, a method is provided for preparing oxazoles of formula I wherein an amide of the structure

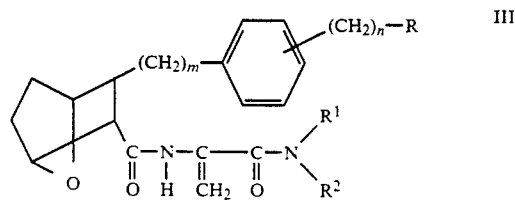

wherein m, n, R, $R^1$ and $R^2$ are as defined above is treated with a bromine source such as $Br_2$ or N-bromosuccinamide followed by treatment with an amine base, such as triethylamine, at a reduced temperature, under an inert atmosphere, such as argon, and then is treated with an organic base to form the bromo-ester compound II, which is then employed as described above to form oxazole I.

Further in accordance with the present invention, a method is provided for preparing oxazoles of formula I wherein a chloromethyl amide of the structure IV

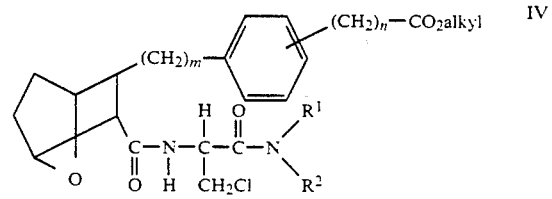

wherein m, n, $R^1$ and $R^2$ are as defined above, is treated with 1,8-diazabicyclo[5.4.0]undec-7-ene (DBU) under an inert atmosphere, such as argon, to form the amide III, which is then employed as described above to form oxazole I.

Still further in accordance with the present invention, a method is provided for forming the starting chloromethyl amide IV wherein a hydroxymethyl compound of the structure V

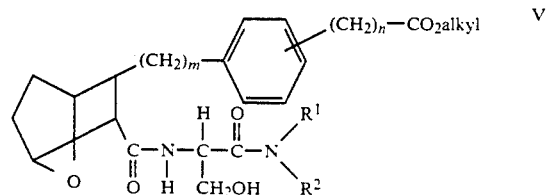

is treated with methanesulfonyl chloride (mesyl chloride) in the presence of an organic base to form the mesylate VI

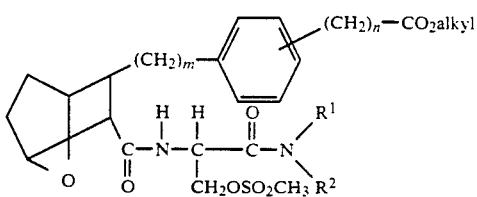

and mesylate VI is subjected to a displacement reaction wherein VI is treated with an alkali metal salt such as lithium chloride or a quaternary ammonium salt such as benzyltributyl ammonium chloride, to form the chloromethyl amide IV.

In an alternative method for preparing the starting chloromethyl amide IV, in accordance with the present invention, an amide of the structure VII (formed from the corresponding amine VIIA)

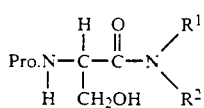

wherein Pro represents a protecting group, and $R^1$ and $R^2$ are as defined above, is treated with an organic base and methanesulfonyl chloride at a reduced temperature to form the mesylate VIII.

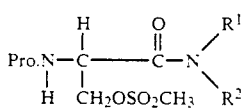

Mesylate VIII is subjected to a displacement reaction wherein VIII is treated with an alkali metal salt such as lithium chloride or a quaternary ammonium salt such as benzyltributyl ammonium chloride, at an elevated temperature to form chloromethyl compound IX

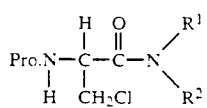

chloromethyl compound IX is treated with a deprotecting agent to form the chloromethyl amine X

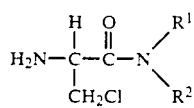

and X is coupled with acid XI

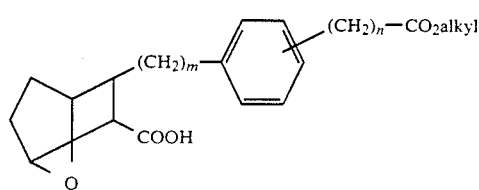

in the presence of 1-(3-dimethylaminopropyl)-3-ethylcarbodiimide hydrochloride (WSC) or dicyclohexylcarbodiimide (DCC), and 1-hydroxybenzotriazole (HOBT), in the presence of N-methylmorpholine (NMM), to form the chloromethylamide IV.

Alternatively, the acid XI can be converted to the corresponding acid chloride by treatment with oxalyl chloride, preferably in the presence of a catalytic amount of N,N-dimethylformamide, which acid chloride is treated with amine X in the presence of an acid scavenger such as triethylamine or DBU, or sodium bicarbonate (when employing aqueous conditions) to form chloromethylamide IV.

DETAILED DESCRIPTION OF THE INVENTION

In carrying out the present invention for preparing oxazoles I, vinyl bromide II is treated with a metal carbonate cyclizing agent of the structure A $$M_2CO_3$$

where M is a Group 5 or 6 alkali metal, that is cesium or rubidum, or a Group 5 or 6 alkaline earth metal, that is strontium or barium, preferably cesium, alone or optionally with a Group 2 to 4 alkali metal carbonate, such as lithium carbonate, sodium carbonate or potassium carbonate, in the presence of an inert organic solvent such as dioxane, tetrahydrofuran (THF), ethyl acetate, toluene, or acetonitrile, preferably dioxane, at a temperature within the range of from about 25° to about 80° C., and preferably from about 30° to about 65° C. The cyclizing agent A will be employed in a molar ratio to the vinyl bromide II of within the range of from about 0.75: to about 5:1, and preferably from about 1:1 to about 3:1.

Preferred vinyl bromide starting materials will comprise those of Formula II wherein m is 1 or 2 and n is 1, 2 or 3, $R^1$ is alkyl of from 3 to 7 carbons and $R^2$ is hydrogen or alkyl of from 3 to 7 carbons.

Where the oxazole I is prepared starting with amide III, amide III will be treated with a bromine source such as $Br_2$ or N-bromosuccinamide, preferably $Br_2$, at a reduced temperature of within the range of from about $-80°$ to about $-40°$ C., and preferably from about $-80°$ to about $-60°$ C., under an inert atmosphere such as argon or nitrogen, preferably argon, employing a molar ratio of bromine source to amide III of within a range of from about 1:1 to about 2:1 and preferably from about 1:1 to about 1.1:1. The organic base, which may be triethylamine, DBU, Hunig's base (diisopropylethyl amine), collidine, dimethylamino pyridine or pyridine, preferably triethylamine, will be admixed with the reaction mixture at a temperature of within the range of from about $-78°$ C. to about 25° C. and preferably from about $-20°$ C. to about 0° C. The above reactions will be carried out in the presence of an inert organic solvent such as methylene chloride, chloroform, tetrahydrofuran (THF), acetonitrile, or acetone, preferably methylene chloride.

Where the oxazole I is prepared starting with the chloromethylamide IV, DBU will be employed in a molar ratio to amide IV of within the range of from about 1:1 to about 4:1, preferably from about 1:1 to about 2:1, and the reaction will be carried out under an inert atmosphere such as argon or nitrogen, preferably argon.

In a first method for preparing the starting chloromethyl amide IV, hydroxymethyl compound V (prepared as described in U.S. application Ser. No. 540,026, filed Jun. 18, 1990 now U.S. Pat. No. 5,100,889) will be treated with mesyl chloride employing a molar ratio of mesyl chloride to amide IV of within the range of from about 1:1 to about 3:1, and preferably from about 1:1 to about 1.5:1, in the presence of an organic base such as triethylamine or pyridine, preferably triethylamine, in the presence of an inert organic solvent such as methylene chloride or THF, at a temperature of within a range of from about −78° C. to about 0° C. and preferably from about −20° C. to about 0° C.

The mesylate VI will be subjected to a displacement reaction by treatment with an alkali metal salt such as lithium chloride, sodium chloride, potassium chloride, lithium bromide or sodium iodide, preferably lithium chloride, or with a quaternary ammonium salt such as benzyltributyl ammonium chloride, tetra-n-butylammonium bromide, or tetra-n-butylammonium iodide, employing a molar ratio of salt to VI within the range of from about 2:1 to about 10:1, preferably from about 2:1 to about 5:1, the above reaction being carried out in the presence of an inert organic solvent such as dimethylformamide, THF, acetone, chloroform or methylene chloride, preferably dimethylformamide or methylene chloride.

In the alternative method for preparing the starting chloromethyl amide IV, the staring amide VII (prepared as described in U.S. application Ser. No. 540,026, filed Jun. 18, 1990 now U.S. Pat. No. 5,100,889) will include a protecting group which can be t-butyloxycarbonyl (BOC) or trichloroethoxy carbonyl, preferably BOC, and will be treated with an organic base such as triethylamine, or pyridine, preferably triethylamine, and methanesulfonyl chloride at a reduced temperature of within the range of from about −78° C. to about 0° C. and preferably from about −20° C. to about 0° C. to form the mesylate VIII. The methanesulfonyl chloride will be employed in a molar ratio to amide VII of within the range of from about 1:1 to about 5:1, preferably from about 1:1 to about 2:1.

The mesylated compound VIII will then be subjected to to a displacement reaction employing an alkali metal salt such as lithium chloride, sodium chloride, potassium chloride, preferably lithium chloride, which is reacted with VIII at an elevated temperature of from about 40° C. to about 100° C., and preferably from about 40° C. to about 65° C., to form the chloromethyl compound IX. The alkali metal salt will be employed in a molar ratio to VIII of within the range of from about 2:1 to about 10:1, preferably from about 2:1 to about 5:1.

The chloromethyl compound IX will be deprotected by reaction with a deprotecting agent such as trifluoroacetic acid, anhydrous hydrogen chloride or HCl/dioxane, preferably trifluoroacetic acid, employing a molar ratio of deprotecting agent to IX of within the range of from about 5:1 to about 20:1, preferably from about 5:1 to about 10:1 to form the chloromethyl amine compound X.

Chloromethyl amine X is coupled with acid XI employing a molar ratio of X:XI of within the range of from about 1:1 to about 3:1, preferably from about 1:1 to about 1.5:1. The coupling reaction is carried out in the presence of 1-(3-dimethylaminopropyl)-3-ethylcarbodiimide hydrochloride (WSC) or dicyclohexylcarbodiimide (DCC) and 1-hydroxybenzotriazole (HOBT) in the presence of N-methylmorpholine (NMM), employing a molar ratio of WSC or DCC:XI of within the range of from about 1:1 to about 3:1, preferably from about 1:1 to about 1.5:1. The HOBT will be employed in a molar ratio to WSC or DCC of within the range of from about 1:1 to about 3:1, preferably from about 1:1 to about 1.5:1 while the NMM will be employed in a molar ratio to HOBT of within the range of from about 2:1 to about 5:1, preferably from about 2:1 to about 3:1. The above reaction will be carried out at a temperature within the range of from about −20° C. to about 40° C. and preferably from about 0° C. to about 25° C.

Alternatively, acid XI may be activated by forming a mixed anhydride, mixed carbonate, or preferably acid chloride (by known literature methods), using a slight excess (of from about 10 to about 50%) of amine and acid scavenger relative to the acid chloride. A reaction temperature of from about −78° to about 0° C. will be employed.

The term "lower alkyl" or "alkyl" as employed herein includes both straight and branched chain radicals of up to 18 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1, 2 or 3 halo substituents, an aryl substituent, an alkyl-aryl substituent, a haloaryl substituent, a cycloalkyl substituent, an alkylcycloalkyl substituent, hydroxy or a carboxy substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with substituents such as halogen, lower alkyl, alkoxy and/or hydroxy group.

The term "aryl" or "Ar" as employed herein refers to monocyclic or bicyclic aromatic groups containing from 6 to 10 carbons in the ring portion, such as phenyl, naphthyl. Aryl (or Ar), phenyl or naphthyl may include substituted aryl, substituted phenyl or substituted naphthyl, which may include 1 or 2 substituents on either the phenyl or naphthyl such as lower alkyl, trifluoromethyl, halogen (Cl, Br, I or F), lower alkoxy, arylalkoxy, hydroxy, alkylthio, alkylsulfinyl, alkylsulfonyl, arylthio, arylsulfinyl and/or arylsulfonyl.

The term "aralkyl", "aryl-alkyl" or "aryl-lower alkyl" as used herein refers to lower alkyl groups as discussed above having an aryl substituent, such as benzyl.

The term "lower alkoxy", "alkoxy" or "aralkoxy" includes any of the above lower alkyl, alkyl or aralkyl groups linked to an oxygen atom.

The term "halogen" or "halo" as used herein refers to chlorine, bromine, fluorine or iodine with chlorine being preferred.

The term "lower alkenyl" or "alkenyl" as employed herein with respect to the $R^1$ substituent includes a carbon chain of up to 16 carbons, preferably 3 to 10 carbons, containing one double bond which will be separated from "N" by at least one saturated carbon moiety such as $-(CH_2)_q-$ where q can be 1 to 14, such as 2-propenyl, 2-butenyl, 3-butenyl, 2-pentenyl, 4-pentenyl and the like, and may include a halogen substituent such as I, Cl, or F.

The term "lower alkynyl" or "alkynyl" as employed herein with respect to the $R^1$ substituent includes a carbon chain of up to 16 carbons, preferably 3 to 10 carbons, containing one triple bond which will be separated from "N" by at least one saturated carbon moiety such as —(CH$_2$)$_{q'}$— where q' can be 1 to 14, such as 2-propynyl, 2-butynyl, 3-butynyl and the like.

The term "cycloheteroalkyl" as used herein as an R$^1$ substitutent refers to a 5-, 6- or 7-membered saturated ring which includes 1 or 2 hetero atoms such as nitrogen, oxygen and/or sulfur, and which is linked to the "N" of the

group through a carbon atom either beta or gamma to a heteroatom, such as

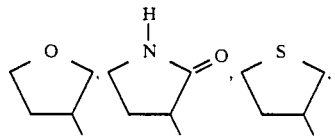

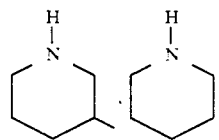

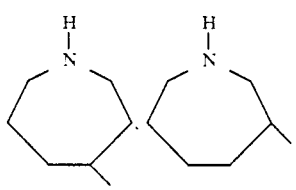

and the like.

The term "heteroaryl" or heteroaromatic as an R$^1$ substitutent refers to a 5- or 6-membered aromatic ring which includes 1 or 2 hetero atoms such as nitrogen, oxygen or sulfur, which are not directly linked through a hetero atom to the "N" of the

group, such as

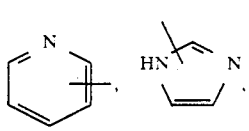

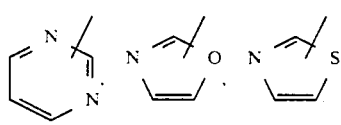

and the like

The term "cycloheteroalkylalkyl" as defined by R$^1$ refers to 5-, 6- or 7-membered saturated ring which includes 1 or 2 heteroatoms such as nitrogen, oxygen or sulfur, and is linked to the "N" of the

group through a (CH$_2$)$_x$ chain wherein x is 1 to 12, preferably 1 to 8, such as

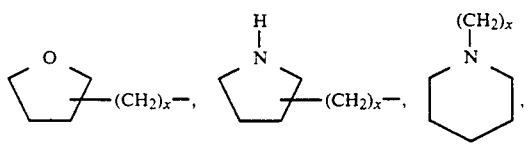

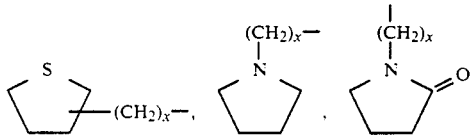

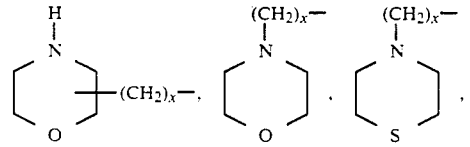

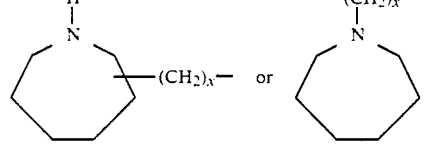

The term "heteroarylalkyl" as defined by R$^1$ refers to a 5-, 6- or 7-membered aromatic ring which includes 1, 2, 3 or 4 heteroatoms such as nitrogen, oxygen or sulfur, and is linked to the "N" of the

group through a —(CH$_2$)$_{x'}$— chain where x' is 1 to 12, preferably 1 to 8, such as

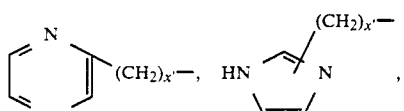

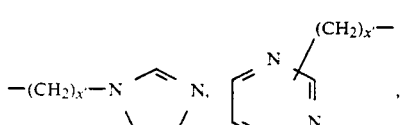

-continued

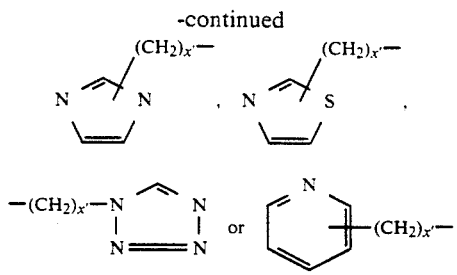

Preferred compounds prepared in accordance with the method of the invention are those compounds of formula I wherein m is 1, n is 1 or 2, R is $CO_2H$, $R^1$ is substituted alkyl or a cycloheteroalkylalkyl and $R^2$ is H or lower alkyl, and $-(CH_2)_n-CO_2alkyl$ is in the ortho or meta position.

The following examples represent preferred embodiments of the invention.

EXAMPLE 1

N-Pentyl-L-serinamide 1:1 oxalate salt

A

N-Pentyl-N2-[(phenylmethoxy)carbonyl]-L-serinamide

A 5-L, 3-necked flask was charged with N-CBZ-L-serine (110 g, 0.46 mole) (CBZ=carbobenzyloxy) followed by dichloromethane (2.1 L). The resulting slurry was stirred under argon and treated with triethylamine (61.7 mL, 0.443 mole) over several minutes. The resulting hazy solution was cooled to an internal temperature of $-35°$ and treated over 10 min with trimethylacetylchloride (51.06 mL, 0.415 mole) such that the internal temperature did not rise above $-30°$. The reaction was stirred an additional 40 min at $-25°$ to $-30°$, treated with pyridine (35.2 mL, 0.435 mole) over 5 min and stirred an additional 10 min. Amylamine (51 mL, 0.44 mole) was added over 10 min while maintaining the internal temperature at $-25°$ to $-29°$. The reaction was stirred for 30 min while warming to $-25°$. A precipitate formed during this warming. The reaction was further warmed to $-10°$ over 40 min during which time the precipitate redissolved. After stirring an additional 20 min at $-10°$, the reaction was quenched by the addition of 500 mL of 1N HCl. The biphasic mixture was stirred for 20 min and transferred to a separatory funnel. The aqueous layer was extracted with dichloromethane (2×75 mL). The combined dichloromethane solutions were concentrated in vacuo to a weight of 500 g. Ethyl acetate (EtOAc) (2.25 L) was added and the organic solution was washed with 1N HCl (2×400 mL) and 1N $K_2CO_3$ (1×700 mL and 2×500 mL). The organic solution was dried (magnesium sulfate), filtered and concentrated in vacuo to the title compound which was used in the next step without purification.

B. N-Pentyl-L-serinamide, 1:1 oxalate salt

The part A compound was evaporated from 95% ethanol (EtOH) to remove residual solvents. The residue was dissolved in 95% EtOH (1.28 L) and treated under nitrogen with 20% $Pd(OH)_2$ (12.8 g). The mixture was stirred and sparged with hydrogen. After 2.5 h the catalyst was filtered off and washed with 95% EtOH. The filtrate was concentrated in vacuo to 73.1 g. A portion of this material (36.3 g, 0.21 mole) was redissolved in 95% EtOH (221 mL) and added slowly to a stirred room temperature solution of oxalic acid dihydrate (31.5 g, 0.25 mole) in 95% EtOH (221 mL). After the addition the resulting slurry was further diluted with 120 mL of 95% EtOH, stirred an additional 30 min and then heated to reflux. The slurry was treated with water (29 mL) to afford a clear, light yellow solution. After stirring an additional 40 min the heat was removed and the solution cooled. The resulting slurry was stirred at ambient temperature for 18 h, filtered and washed with 95% EtOH (1×72 mL, and 1×48 mL) and hexane (2×48 mL). Drying in vacuo produced 42.9 g (77.3%) of the title compound, mp 174° C.

EXAMPLE 2

[1S-(1α,2α,3α,4α)]-2-[[3-[4-[(Pentylamino)-carbonyl]-2-oxazolyl]-7-oxabicyclo[2.2.1]hept-2-yl]methyl]benzenepropanoic acid, methyl ester

A.

[1S-[1α,2α,3α(R*),4α]]-2-[[3-[[[1-(Hydroxymethyl)-2-oxo-2-(pentylamino)ethyl]amino]carbonyl]-7-oxabicyclo[2.2.1]hept-2-yl]methyl]benzenepropanoic acid, methyl ester To a stirred solution of [1S-(1α,2α,3α,4α)]-2-[(3-carboxy-7-oxabicyclo[2.2.1]hept-2-yl)methyl]benzenepropanoic acid, methyl ester (prepared as described in U.S. Pat. No. 5,100,889) (17.6 g, 55.3 mmol) and 4-methylmorpholine (12.2 mL, 111 mmol) in 100 mL of DMF under argon at $-10°$ C. was added dropwise isobutylchloroformate (7.94 mL, 61.2 mmol) over a 15 min period. This solution was stirred at $-10°$ C. for 50 min at which time n-pentyl-L-serinamide (10.6 g, 57.5 mmol) was added. The reaction mixture was stirred at $-10°$ C. for 1 hour and at room temperature for 16 hours. This mixture was diluted with 2 L of ethyl acetate (EtOAc) and washed with 1N HCl solution (2×600 mL), saturated $NaHCO_3$ solution (1×600 mL) and brine (1×600 mL). The EtOAc layer was dried ($MgSO_4$), filtered and concentrated in vacuo. This was triturated in 600 mL of 1:1 ether-hexane to give 25.2 g (96%) of title amide.

TLC: silica gel, 4% $CH_3OH/CH_2Cl_2$, $R_f$ 0.38, Cerium dip.

$A^1$. Alternative Procedure for Forming A

A solution of Part A acid ester starting material (30.27 g, 95.06 mmol) and DMF (1.5 mL, 19.37 mmol) in $CH_2Cl_2$ (200 mL) was cooled to an internal temperature of 0° C. under an argon atmosphere. To the above solution was added oxalyl chloride (9.1 mL, 104.57 mmol) over ~2.5 minutes. After 2 hours, gas evolution had ceased. A 75 μL aliquot was removed and quenched into MeOH. TLC analysis of this solution showed no remaining starting acid, thus indicating complete conversion to the acid chloride. Toluene (30 mL) was added to the reaction mixture. The crude acid chloride solution was partially concentrated to an oil/solid mixture (43.37 g).

In a separate flask, a suspension of N-pentyl-L-serinamide oxalate salt (30.26 g, 114.50 mmol) in $CH_2Cl_2$ (200 mL) was treated sequentially, under argon, with DBU (33.4 mL, 223.28 mmol) and $Et_3N$ (16.0 mL, 114.50 mmol). The resulting solution was cooled to $-78°$ C. The crude acid chloride was redissolved in $CH_2Cl_2$ (350 mL), cooled to 8° C. under argon, and added to the solution of the amine via cannula such that the reaction temperature never exceeded $-72°$ C. The addition process required 35 minutes. The flask containing the acid chloride solution was rinsed with $CH_2Cl_2$ (30 mL)

which was transferred to the reaction mixture. After 45 minutes an aliquot was removed and quenched into MeOH. TLC analysis of the solution showed no evidence of unreacted acid chloride; only Part A title compound and a trace of starting acid were present. The dry ice/acetone bath was removed and with vigorous stirring, 1N HCl (500 mL) was immediately added. The internal temperature quickly rose to −10° C. After transferring to a separatory funnel, additional water (1 L) and $CH_2Cl_2$ (250 mL) were added. The layers were mixed and split. The aqueous layer was extracted with $CH_2Cl_2$ (250 mL). The organic phases were combined and washed with 1N HCl (250 mL) and saturated aqueous $NaHCO_3$ (500 mL). The aqueous $NaHCO_3$ solution was back-extracted with $CH_2Cl_2$ (250 mL). The organic solutions were combined, washed again with saturated aqueous $NaHCO_3$ (250 mL) and saturated aqueous NaCl (500 mL), dried ($MgSO_4$), filtered, concentrated, and left under high vacuum for 12 hours to give the crude title compound (44.27 g).

A portion of this material (38.27 g) was placed in a flask with water (7.25 mL) and EtOAc (344 mL) and the mixture was brought to a boil. The resulting clear yellow solution was allowed to cool to room temperature and stand for 22 hours. EtOAc (125 mL) was added to slurry the all-engulfing white solid and the crystals were recovered via filtration. The white crystals were washed sequentially with EtOAc (2×75 mL) and hexanes (1×200 mL), air dried (1.5 hours), and placed under high vacuum for 24 hours to give the title compound (33.87 g).

Procedure I for B. and C.

B.

[1S-[1α,2α,3α(R*),4α]]-2-[[3-[[[1-[(Methylsulfonyl)oxymethyl]-2-oxo-2-(pentylamino)ethyl]amino]carbonyl]-7-oxabicyclo[2.2.1]hept-2-yl]methyl]benzenepropanoic acid, methyl ester and

C.

[1S-[1α,2α,3α(R*),4α]]-2-[[3-[[[1-(Chloromethyl)-2-oxo-2-(pentylamino)ethyl]amino]carbonyl]-7-oxabicyclo[2.2.1]hept-2-yl]methyl]benzenepropanoic acid, methyl ester To a stirred solution of Part A amide (25.2 g, 53.2 mmol) in 480 mL of dry $CH_2Cl_2$ at −10° C. under argon was added, in order, triethylamine ($Et_3N$) (8.88 mL, 63.8 mmol) and methanesulfonyl chloride (4.53 mL, 58.5 mmol). This solution was stirred at −10° C. for 15 minutes and diluted with 200 mL of $CH_2Cl_2$. This mixture was washed with ice-cold 1N HCl solution (2×150 mL) and a 1:1 mixture of saturated $NaHCO_3$ solution and brine (1×150 mL). The organic layer was dried ($MgSO_4$), filtered and concentrated in vacuo to give solid intermediate Part B mesylate. To a stirred solution of this Part B mesylate in 120 mL of DMF was added anhydrous lithium chloride (5.58 g, 133 mmol). An exotherm was noted. This solution was stirred at room temperature for 18 hours and then diluted with 1 L of $CH_2Cl_2$. The solution was washed with 10% LiCl solution (2×250 mL), water (2×250 mL), saturated $NaHCO_3$ solution (1×250 mL) and brine (1×250 mL). The organic layer was dried ($MgSO_4$), filtered and concentrated in vacuo to give Part C chloride (26.2g, 100% crude yield).

TLC: silica gel, 3:1 EtOAc-hexane, $R_f$ 0.72, cerium dip. mp 180°−182° C.

$[α]_D = −5.5°$ (c=0.9, $CHCl_3$).

Anal. Calc'd for $C_{26}H_{37}N_2O_5Cl$:
C, 63.34; H, 7.56; N, 5.68; Cl, 7.19
Found: C, 63.39; H, 7.68; N, 5.69; Cl, 7.36.

Alternative Procedure II for B. and C.

To a stirred solution of Part A amide (25.2 g, 53.2 mmol) in 250 mL of dry $CH_2Cl_2$ at −10° C. under argon is added, in order, triethylamine ($Et_3N$) (8.88 mL, 63.8 mmol) and methanesulfonyl chloride (4.53 mL, 58.5 mmol). This solution is stirred at −10° C. for 15 minutes and diluted with 100 mL of DMF. To this mixture is added anhydrous lithium chloride (5.58 g, 133 mmol) in 50 mL DMF. This solution is stirred at room temperature for 18 hours and then diluted with 1 L of $CH_2Cl_2$. The solution is washed with 10% LiCl solution (2×250 mL), water (2×250 mL), saturated $NaHCO_3$ solution (1×250 mL) and brine (1×250 mL). The organic layer is dried ($MgSO_4$), filtered and concentrated in vacuo to give Part C chloride.

Alternative Procedure III for B. and C.

To a stirred solution of Part A amide (25.2 g, 53.2 mmol) in 350 mL of dry $CH_2Cl_2$ at −10° C. under argon is added, in order, triethylamine ($Et_3N$) (8.88 mL, 63.8 mmol) and methanesulfonyl chloride (4.53 mL, 58.5 mmol). This solution is stirred at −10° C. for 15 minutes and diluted with 200 mL of $CH_2Cl_2$. This mixture is washed with ice-cold 1N HCl solution (2×150 mL) and a 1:1 mixture of saturated $NaHCO_3$ solution and brine (1×150 mL). The organic layer is dried ($MgSO_4$), filtered and concentrated in vacuo to give solid intermediate Part B mesylate. To a stirred solution of this Part B mesylate in 250 mL of $CH_2Cl_2$ portionwise is added benzyltributylammonium choride (33 g, 107 mmol). This solution is stirred at room temperature for 18 hours and then diluted with 1 L of $CH_2Cl_2$. The solution is washed with 10% LiCl solution (2×250 mL), water (2×250 mL), saturated $NaHCO_3$ solution (1×250 mL) and brine (1×250 mL). The organic layer is dried ($MgSO_4$), filtered and concentrated in vacuo to give Part C chloride.

Alternative Procedure IV for B. and C.

To a stirred solution of Part A amide (25.2 g, 53.2 mmol) in 250 mL of dry $CH_2Cl_2$ at −10° C. under argon is added, in order, triethylamine ($Et_3N$) (8.88 mL, 63.8 mmol) and methanesulfonyl chloride (4.53 mL, 58.5 mmol). This solution is stirred at −10° C. for 15 minutes. To this mixture is added portionwise solid benzyltributylammonium chloride (33.0 gm, 107 mmol). This solution is stirred at room temperature for 18 hours and then diluted with 1 L of $CH_2Cl_2$. The solution is washed with 10% LiCl solution (2×250 mL), water (2×250 mL), saturated $NaHCO_3$ solution (1×250 mL) and brine (1×250 mL). The organic layer is dried ($MgSO_4$), filtered and concentrated in vacuo to give Part C chloride.

D.

[1S-[1α,2α,3α(R*),4α]]-2-[[3-[[[1-Methylene-2-oxo-2-(pentylamino)ethylamino]carbonyl-7-oxabicyclo[2.2.1]hept-2-yl]methyl]benzenepropanoic acid, methyl ester To a stirred solution of Part C chloride (26.2 g, 53.2 mmol) in 740 mL of dry $CH_2Cl_2$ under argon was added DBU (15.0 mL, 106 mmol). The reaction mixture was stirred at room temperature for 4.5 hours and washed with 1N HCl solution (2×400 mL), half-saturated $NaHCO_3$ solution (1×400 mL) and brine (1×400 mL).

The organic layer was dried (MgSO4), filtered and concentrated in vacuo to give 26 g of crude oil. This crude oil (25 g) was chromatographed on 900 g of Merck silica gel 60 using 2 L of 40% EtOAc in hexane and 6 L of 50% EtOAc in hexane as eluants to give 17.4 g (72%) of title olefin as a viscous oil.

$[\alpha]_D = +27.7°$ (c=1.0, CH$_3$OH).

TLC: silica gel, 2:1 EtOAc-hexane, R$_f$ 0.64, cerium dip.

Anal. Calc'd for C$_{26}$H$_{36}$N$_2$O$_5$:
C, 68.40; H, 7.95; N, 6.14
Found: C, 68.10; H, 8.12; N, 5.87.

This olefin was stored at $-78°$ C. under argon.

E.
[1S-[1α,2α,3α(R*,E),4α]]-2-[[3-[[[1-(Bromomethylene)-2-oxo-2-(pentylamino)ethyl]amino]carbonyl]-7-oxabicyclo[2.2.1]hept-2-ylmethyl]benzenepropanoic acid, methyl ester and

F.
[1S-[1α,2α,3α(R*,Z),4α]]-2-[[3-[[[1-(Bromomethylene)-2-oxo-2-(pentylamino)ethyl]amino]carbonyl]-7-oxabicyclo[2.2.1]hept-2-yl]methyl]benzenepropanoic acid, methyl ester To a stirred solution of purified Part D olefin (13.8 g, 30.3 mmol) in 500 mL of dry CH$_2$Cl$_2$ under argon at $-78°$ C. was added bromine (1.58 mL, 30.7 mmol). At the end of the addition of bromine the reaction mixture became bright yellow. This yellow solution was stirred at $-78°$ C. for 15 minutes and treated slowly with triethylamine (16.8 mL, 121 mmol). The reaction flask was then transferred to a wet ice bath and stirred for 40 minutes. The mixture was diluted with 200 mL of CH$_2$Cl$_2$ and washed with 2% NaHSO$_3$ solution (2×250 mL), water (1×250 mL) and brine (1×250 mL). The organic layer was dried (MgSO$_4$), filtered and concentrated in vacuo. This was triturated with 1 L of 3:7 hexane-ether to give 14.9 g (92% or 66% from starting methyl ester used in Part A) of 9:1 mixture of title vinyl bromides E (major) and F (minor).

TLC: silica gel, 1:2 hexane-EtOAc, R$_f$, 0.31, 0.56, UV & cerium dip.

HPLC: R$_T$=6.3 minutes (87%) and 7.2 minutes (9.5%), linear gradient of 72-90% aqueous methanol containing 0.2% H$_3$PO$_4$, 20 minutes, detected at 217 nm, YMC S-3 (ODS), 6.0×150 mm, 3 micron spherical end capped column, flow rate 1.5 mL/minute.

The product from a smaller scale reaction (1.9 mmol) was purified and separated by chromatography on silica gel (150 mL, Merck), eluting with ethyl acetate:hexane (1:1 and 1:2) and finally with ethyl acetate to give the two isomers E and F. The minor isomer F was obtained as a white solid (94 mg, 9.2%). mp. 104°-108° C.

$[\alpha]_D = +46.0°$ (c=0.7, CHCl$_3$).

Anal. Calc'd for C$_{26}$H$_{35}$N$_2$O$_5$Br:
C, 58.32; H, 6.59; N, 5.23; Br, 14.92
Found: C, 58.18; H, 6.66; N, 4.99; Br, 15.14.

The major isomer E was also a white solid (877 mg, 86%). mp. 160°-164° C.

$[\alpha]_D = -37.9°$ (c=1.0 CHCl$_3$).

Anal. Calc'd for C$_{26}$H$_{35}$N$_2$O$_5$Br:
C, 58.32; H, 6.59; N, 5.23; Br, 14.92
Found: C, 58.28; H, 6.64; N, 4.96; Br, 15.19.

Alternate E and F preparation

To a stirred solution of crude Part C olefin (olefin was worked up as described in the above preparation and used without purification by column chromatography, 1.10 g) in 42 mL of dry CH$_2$Cl$_2$ under argon at $-78°$ C. was added bromine over 10 minutes. Bromine was added until a bright yellow color appeared and stayed in the reaction mixture. The amount of bromine used in this scale was 125 μL. The mixture was stirred at $-78°$ C. for 5 minutes and treated with Et$_3$N (1.33 mL, 9.60 mmol). The reaction flask was then moved to a wet-ice bath and stirred for 30 minutes. The mixture was diluted with 100 mL of CH$_2$Cl$_2$ and washed with 2% NaHSO$_3$ solution (2×60 mL), water (1×60 mL) and brine (1×60 mL). The organic layer was dried (MgSO$_4$), filtered and concentrated in vacuo. This was triturated in 50 mL of ether to give 716 mg (57% from starting acids used in Part A) of a 9:1 mixture of vinyl bromides E and F.

TLC silica gel 1:2 hexane-EtOAc, R$_f$, Part E compound, 0.31, Part F compound, 0.56, cerium dip.

TLC of the mother liquor indicated that the vinyl bromides were the major components in this mixture.

G.
[1S-(1α,2α,3α,4α)]-2-[[3-[4[(Pentylamino)carbonyl]-2-oxazolyl]-7-oxabicyclo[2.2.1]hept-2-yl]methyl]benzenepropanoic acid, methyl ester Vinyl bromides E and F (3.21 g, 6 mmol, 1 eq., mixture of isomers) were dissolved in 1,4-dioxane (90 mL, Burdick and Jackson, stored over activated sieves) and treated with cesium carbonate (3.17 g, 6 mmol, 1 eq.) in an argon atmosphere. The mixture was stirred while heating in an oil bath maintained at 50°-53° C. for 23 hours. The reaction was cooled and diluted with ethyl acetate (400 mL). The ethyl acetate solution was washed with water (100 mL) and saturated sodium chloride solution (100 mL), dried (MgSO$_4$), and freed of solvent in vacuo leaving a semi-solid (3.40 g). This was stirred with ethyl ether (25 mL) for 1 hour and then cooled at $-20°$ C. for 1 hour. Solid title oxazole was harvested by filtration and washed with cold ether to give title compound, (1.346 g, 49.4%), mp. 133°-136° C.

$[\alpha]_D = +15.4°$ (c=1.0, CHCl$_3$).

Anal Calc'd for C$_{26}$H$_{34}$N$_2$O$_5$:
C, 68.70; H, 7.54; N, 6.16
Found: C, 68.68; H, 7.73; N, 6.19.

HPLC: R$_T$=9.1 min., linear gradient of 72-90% aqueous methanol containing 0.2% H$_3$PO$_4$, 20 min., detected at 217 nm, YMC S-3 (ODS), 6.0×150 mm, 3 micron spherical end capped column, flow rate 1.5 mL/min.

Additional title oxazole (0.308 g, 11.3%) was obtained by silica gel (150 mL. Merck) column chromatography of the mother liquor (eluting solvent—15% acetone in ethyl acetate).

EXAMPLE 3

[1S-[1α,2α,3α(R*),4α]]-2-[[3-[[[1-(Chloromethyl)-2-oxo-2-(pentylamino)ethyl]amino]carbonyl]-7-oxabicyclo[2.2.1]hept-2-yl]methyl]benzenepropanoic acid, methyl ester

A.
(S)-[1-(Hydroxymethyl)-2-oxo-2-(pentylamino)ethyl]-carbamic acid, 1,1-dimethylethyl ester N-Methylmorpholine (NMH) (2.2 g, 20 mmol) was added to a stirred solution of N$^\alpha$-t-BOC-L-serine 4.12 g, 20 mmol), n-amylamine (2.25 g, 25.9 mmol) and N-hydroxybenzotriazole (HOBT) (2.8 g, 20 mmol) in dimethylformamide (DMF) (25 mL) at 0°-5° C. After a few minutes, WSC (3.8 g, 20 mmol) was added. The suspension was stirred at 0° C. to room temperature overnight. It was diluted with EtOAc (150 mL) and washed with 1N aqueous HCl solution (30 mL, 2 times), aqueous sodium bicarbonate solution (50 mL, 2 times), dried (MgSO$_4$), filtered and concentrated to obtain title alcohol (4.85 g, 88% crude) as a light yellow solid.

B.

(S)-[1-[[(Methylsulfonyl)oxy]methyl]-2-oxo-2-(pentylamino)ethyl]carbamic acid, 1,1-dimethylethyl ester Methanesulfonyl chloride (2.8 mL) was added dropwise to a stirred solution of Part A alcohol (4.5 g, 16.42 mmol), triethylamine (1.54 mL, 20 mmol) in dichloromethane (25 mL) at −10° C. After 30 minutes, the mixture was diluted with ethyl acetate (EtOAc) (75 mL) and washed with water (30 mL), 1N HCl solution (30 mL) and saturated brine (30 mL). The EtOAc extract was dried (MgSO$_4$), filtered and concentrated to obtain title mesylate (5.25 g, 91% crude) as an off-white solid.

C.

(R)-[1-(Chloromethyl)-2-oxo-2-(pentylamino)ethyl]carbamic acid, 1,1-dimethylethyl, ester A solution of Part B mesylate (5.2 g, 14.77 mmol) and anhydrous lithium chloride (2 g, 47 mmol) in DMF (25 mL) was heated to 50°-52° C. for 30 hours. The mixture was cooled to room temperature, diluted with EtOAc (100 mL) and washed with water (50 mL) and 10% aqueous LiCl solution (75 mL, 2 times), dried (MgSO$_4$), filtered and concentrated to obtain title chloromethyl compound (4.15 g, 96% crude) as a yellow oil.

D. (R)-2-Amino-3-chloro-N-pentylpropanamide

A solution of Part C chloromethyl compound (586 mg, 2 mmol) in dichloromethane (10 mL) and trifluoroacetic acid (2 mL) was stirred at room temperature overnight. The mixture was concentrated under reduced pressure and the residual oil was dissolved in EtOAc (30 mL) and washed with saturated NaHCO$_3$ solution (25 mL, 2 solution). The EtOAc extract was dried (MgSO$_4$), filtered and concentrated to obtain title amine (300 mg, 78% crude) as an oil.

E.

[1S[1α,2α,3α(R*),4α]]-2-[[3-[[[1-(Chloromethyl)-2-oxo-2-(pentylamino)ethyl]amino]carbonyl]-7-oxabicyclo[2.2.1]hept-2-yl]methyl]benzenepropanoic acid, methyl ester N-Methyl morpholine (151 mg, 1.5 mmol) was added to a stirred solution of Part D amine (300 mg, 1.5 mmol), [1S-(1α,2α,3α,4α)]-2-[(3-carboxy-7-oxabicyclo[2.2.1-]hept-2-yl)methyl]benzenepropanoic acid, methyl ester (477 g, 1.5 mmol) in DMF (15 mL) at 0°-5° C. After 5 minutes, WSC (300 mg, 1.5 mmol) was added. The suspension was stirred at 0° C. (2 hours) to room temperature overnight. It was diluted with EtOAc (50 mL) and washed with 1N aqueous HCl solution (30 mL, 2 times), 5% aqueous sodium bicarbonate solution (30 mL, 2 times), brine (30 mL), dried (MgSO$_4$), filtered and concentrated to obtain a solid which was diluted with ether (20 mL). The precipitated solid was filtered, washed with ether and dried in vacuo to obtain title chloromethyl compound (455 mg, 67%) as a white solid.

The so-formed chloromethyl compound may be employed to prepare oxazoles of formula I employing the procedure of Example 2.

Following the procedure of Example 2, the following acid and amine starting material may be used employing procedures as described in Example 2 to prepare oxazoles I.

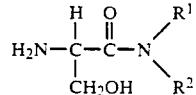

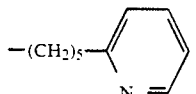

| XI | | | VIIA | |
|---|---|---|---|---|
| m | (CH$_2$)$_n$ n | (position) | R$^1$ | R$^2$ |
| 1 | 0 | (2) | n-C$_4$H$_9$ | n-C$_4$H$_9$ |
| 2 | 1 | (3) | C$_6$H$_5$ | H |
| 1 | 2 | (2) | 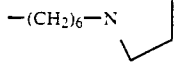 | H |
| 2 | 3 | (4) | 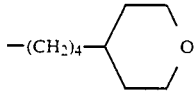 | H |
| 3 | 4 | (2) | 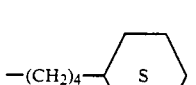 | H |
| 1 | 1 | (2) |  | H |
| 2 | 2 | (3) | —C$_6$H$_{13}$ | CH$_3$ |
| 3 | 3 | (2) | 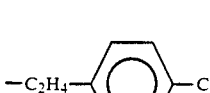 | CH$_3$ |
| 2 | 0 | (2) | 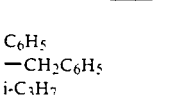 | H |
| 3 | 1 | (3) |  | H |
| 2 | 2 | (2) | C$_6$H$_5$ | C$_6$H$_5$ |
| 1 | 3 | (3) | —CH$_2$C$_6$H$_5$ | H |
| 2 | 4 | (2) | i-C$_3$H$_7$ | H |

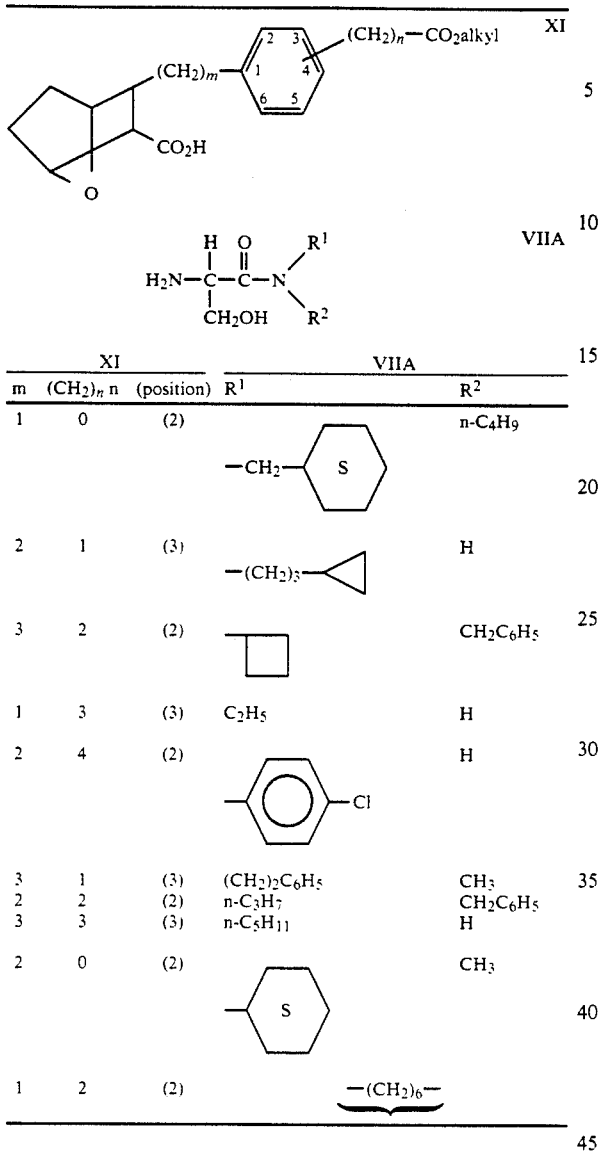

| XI | | | VIIA | |
|---|---|---|---|---|
| m | (CH₂)n | n (position) | R¹ | R² |
| 1 | 0 | (2) | —CH₂—⟨S⟩ | n-C₄H₉ |
| 2 | 1 | (3) | —(CH₂)₃—▷ | H |
| 3 | 2 | (2) | □ | CH₂C₆H₅ |
| 1 | 3 | (3) | C₂H₅ | H |
| 2 | 4 | (2) | ⟨○⟩—Cl | H |
| 3 | 1 | (3) | (CH₂)₂C₆H₅ | CH₃ |
| 2 | 2 | (2) | n-C₃H₇ | CH₂C₆H₅ |
| 3 | 3 | (3) | n-C₅H₁₁ | H |
| 2 | 0 | (2) | —⟨S⟩ | CH₃ |
| 1 | 2 | (2) | —(CH₂)₆— | |

What is claimed is:

1. A method for preparing an oxazole compound having the structure

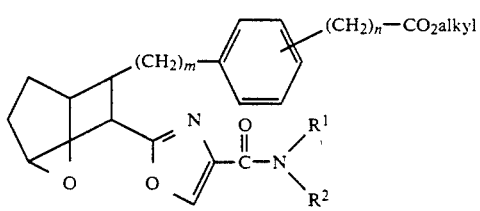

including all stereoisomers thereof, wherein
m is 1, 2 or 3;
n is 0, 1, 2, 3 or 4;
$(CH_2)_n$ is unsubstituted or is substituted with one or two alkyl groups;
R¹ is lower alkyl, aryl, aralkyl, cycloalkyl, cycloalkylalkyl, saturated heterocycle, or aromatic heterocycle; and
R² is hydrogen, lower alkyl, aryl, or aralkyl, or R¹ and R² together with the N to which they are linked form a 5- to 8- membered ring; and which comprises treating a vinyl bromide of the structure

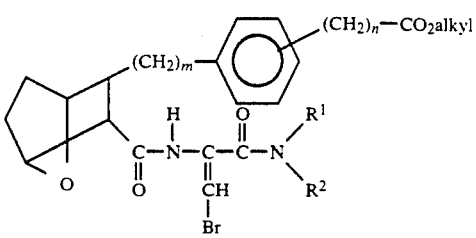

with a cyclizing agent which has the formula $M_2CO_3$ wherein M is a Group 5 or 6 alkali metal or a Group 5 or 6 alkaline earth metal, to form the desired oxazole compound.

2. The method as defined in claim 1 wherein the cyclizing agent is a metal carbonate.

3. The method as defined in claim 1 wherein the cyclizing agent is employed in conjunction with a Group 2 to 4 alkali metal carbonate.

4. The method as defined in claim 3 wherein the Group 2 to 4 alkali metal carbonate is lithium carbonate, sodium carbonate or potassium carbonate.

5. The method as defined in claim 1 wherein the reaction of the vinyl bromide and cyclizing agent is carried out at a temperature of within the range of from about 25° C. to about 80° C.

6. The method as defined in claim 1 wherein the vinyl bromide has the structure

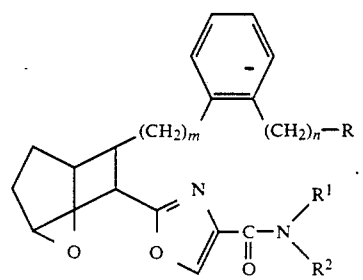

7. The method as defined in claim 6 wherein the final product has the struture

8. The method as defined in claim 7 wherein in the final product one of R¹ and R² is lower alkyl and the other is H.

9. The method as defined in claim 7 wherein in the final product one of R¹ and R² is pentyl and the other is H, m is 1 and n is 2.

10. The method as defined in claim 1 wherein the cyclizing agent is cesium carbonate in a dioxane solvent.

11. A method for preparing an oxazole compound having the structure

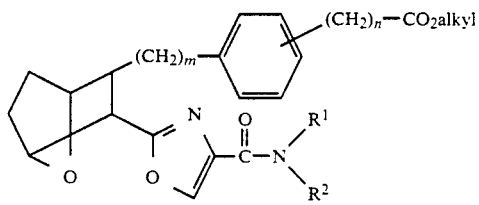

including all stereoisomers thereof, wherein
m is 1, 2 or 3;
n is 0, 1, 2, 3 or 4;
$(CH_2)_n$ is unsubstituted or is substituted with one or two alkyl groups;
R¹ is lower alkyl, aryl, aralkyl, cycloalkyl, cycloalkylalkyl, saturated heterocycle, or aromatic heterocycle; and
R² is hydrogen, lower alkyl, aryl, or aralkyl, or R¹ and R² together with the N to which they are linked form a 5- to 8- membered ring; and which comprises treating an amide of the structure

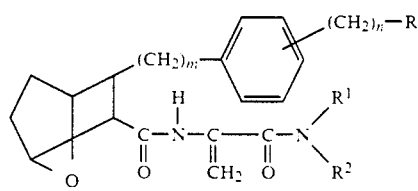

with a bromine source at a reduced temperature, and then with an organic base to form a vinyl bromide of the structure

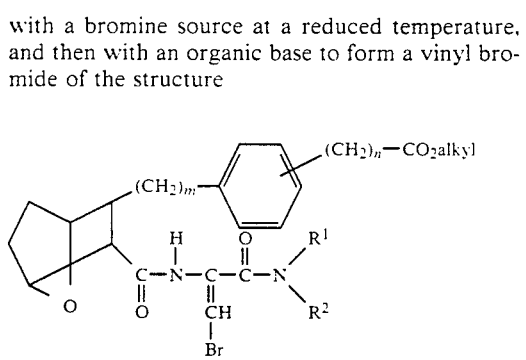

and treating the vinyl bromide with a cyclizing agent which has the formula $M_2CO_3$ wherein M is a Group 5 or 6 alkali metal or a Group 5 or 6 alkaline earth metal to form the desired oxazole compound.

12. The method as defined in claim 11 wherein the cyclizing agent is a metal carbonate.

13. The method as defined in claim 11 wherein the bromine source is bromine and the reaction with bromine is carried out at a temperature of within the range of from about −80° C. to about −25° C.

14. The method as defined in claim 11 wherein the cyclizing agent is employed with a Group 2 to 4 alkali metal carbonate.

15. The method as defined in claim 11 wherein the starting amide has the structure

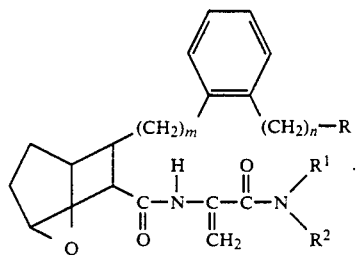

16. The method as defined in claim 11 wherein the final product has the struture

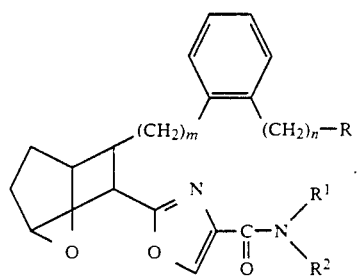

17. The method as defined in claim 11 wherein the cyclizing agent is cesium carbonate.

18. A method for preparing an oxazole compound having the structure

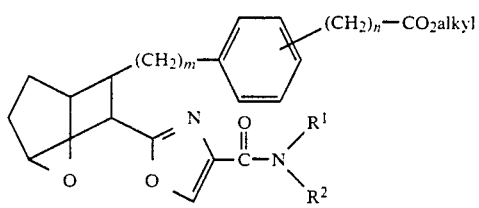

including all stereoisomers thereof, wherein
m is 1, 2 or 3;
n is 0, 1, 2, 3 or 4;
$(CH_2)_n$ is unsubstituted or is substituted with one or two alkyl groups;
R¹ is lower alkyl, aryl, aralkyl, cycloalkyl, cycloalkylalkyl, saturated heterocycle, or aromatic heterocycle; and
R² is hydrogen, lower alkyl, aryl, or aralkyl, or R¹ and R² together with the N to which they are linked form a 5- to 8- membered ring; and which comprises treating a chloromethyl amide of the structure

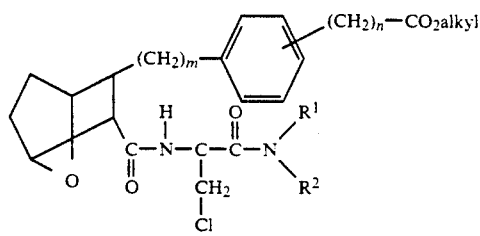

with 1,8-diazabicyclo[5.4.0]undec-7-ene (DBU) to form an amide of the structure

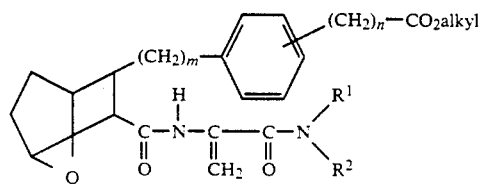

treating the so-formed amide with a bromine source at a reduced temperature and then with an organic amine to form a vinyl bromide of the structure

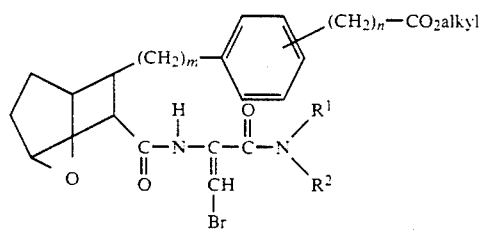

and treating the vinyl bromide compound with a cyclizing agent has the formula $M_2CO_3$ where M is a Group 5 or 6 alkali metal or a Group or 6 alkaline earth metal, to form the desired oxazole compound.

19. The method as defined in claim 18 wherein the cyclizing agent is a metal carbonate.

20. The method as defined in claim 18 wherein the bromine source is bromine and the reaction with bromine is carried out at a temperature of within the range of from about −80° C. to about −25° C.

21. The method as defined in claim 18 wherein the cyclizing agent is employed with a Group 2 to 4 alkali metal carbonate.

22. The method as defined in claim 18 wherein the cyclizing agent is cesium carbonate.

23. The method as defined in claim 18 wherein the starting amide has the structure

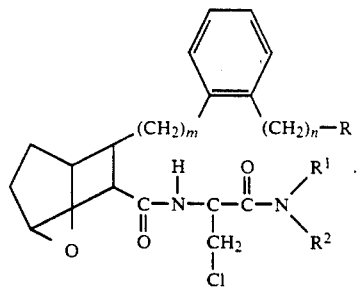

24. The method as defined in claim 18 wherein the final product has the struture

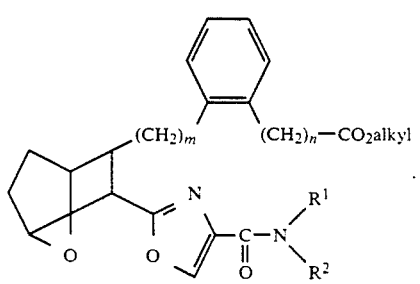

25. A method for preparing an oxazole acid compound having the structure

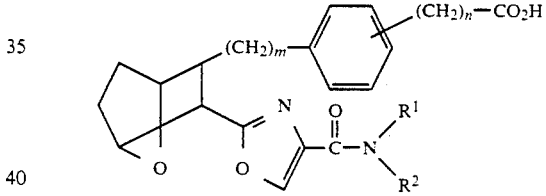

including all stereoisomers thereof, wherein
  m is 1, 2 or 3;
  n is 0, 1, 2, 3 or 4;
  $(CH_2)_n$ is unsubstituted or is substituted with one or two alkyl groups;
  $R^1$ is lower alkyl, aryl, aralkyl, cycloalkyl, cycloalkylalkyl, saturated heterocycle, or aromatic heterocycle; and
  $R^2$ is hydrogen, lower alkyl, aryl, or aralkyl, or $R^1$ and $R^2$ together with the N to which they are linked form a 5- to 8- membered ring; and which comprises treating a vinyl bromide of the structure

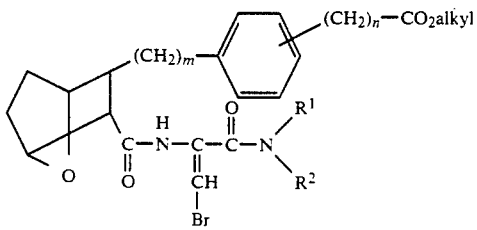

with a cyclizing agent which has the formula $M_2CO_3$ wherein M is a Group 5 or 6 alkali metal or a Group or 6 alkaline earth metal, to form the desired oxazole ester compound, treating the oxazole ester with an alkali metal hydroxide to form the corresponding alkali metal salt, and treating the alkali metal salt with an acid to form the corresponding acid product.

26. The method as defined in claim 25 wherein the cyclizing agent is cesium carbonate.

27. A method for preparing an oxazole acid salt compound having the structure

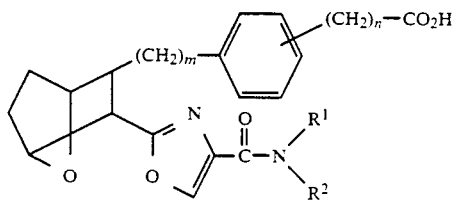

including all stereoisomers thereof, wherein
m is 1, 2 or 3;
n is 0, 1, 2, 3 or 4;
$(CH_2)_n$ is unsubstituted or is substituted with one or two alkyl groups;
$R^1$ is lower alkyl, aryl, aralkyl, cycloalkyl, cycloalkylalkyl, saturated heterocycle, or aromatic heterocycle; and $R^2$ is hydrogen, lower alkyl, aryl, or aralkyl, or $R^1$ and $R^2$ together with the N to which they are linked form a 5- to 8- membered ring; and which comprises treating a vinyl bromide of the structure

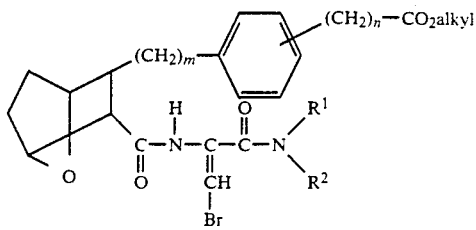

with a cyclizing agent which has the formula $M_2CO_3$ wherein M is a Group 5 or 6 alkali metal or a Group 5 or 6 alkaline earth metal, to form the desired oxazole ester compound, and treating the oxazole ester with an alkali metal hydroxide to form the corresponding alkali metal salt.

28. The method as defined in claim 27 wherein the cyclizing agent is cesium carbonate.

* * * * *

UNITED STATES PATENT AND TRADEMARK OFFICE
CERTIFICATE OF CORRECTION

PATENT NO. : 5,260,448
DATED : November 9, 1993
INVENTOR(S) : Jagabandhu Das et al.

It is certified that error appears in the above-identified patent and that said Letters Patent is hereby corrected as shown below:

Claim 18, column 21, line 50, before the words "or 6", insert -- 5 --.

Claim 25, column 22, line 67, after the word "Group" (second occurrence), insert -- 5 --.

Signed and Sealed this

Fourth Day of October, 1994

Attest:

BRUCE LEHMAN

Attesting Officer          Commissioner of Patents and Trademarks